(12) United States Patent
Masset et al.

(10) Patent No.: US 7,694,548 B2
(45) Date of Patent: Apr. 13, 2010

(54) METHOD AND APPARATUS FOR TESTING AN OBJECT

(75) Inventors: Sylvain Dominique Masset, Seigy (FR); Colin Gordan Hodge, Ellicott City, MD (US)

(73) Assignee: Hamilton Associates, Inc., Owings Mills, MD (US)

( * ) Notice: Subject to any disclaimer, the term of this patent is extended or adjusted under 35 U.S.C. 154(b) by 230 days.

(21) Appl. No.: 11/727,998

(22) Filed: Mar. 29, 2007

(65) Prior Publication Data

US 2008/0236305 A1 Oct. 2, 2008

(51) Int. Cl.
*G01N 15/08* (2006.01)
*G01N 17/00* (2006.01)

(52) U.S. Cl. ................................ 73/37; 73/38; 239/289

(58) Field of Classification Search ............... 73/38, 73/37, 865.6; 239/352, 148, 8, 13, 71, 289
See application file for complete search history.

(56) References Cited

U.S. PATENT DOCUMENTS

| | | | | |
|---|---|---|---|---|
| 2,862,646 | A * | 12/1958 | Hayford et al. | 222/630 |
| 3,328,588 | A * | 6/1967 | Steinberg | 356/338 |
| 3,550,257 | A * | 12/1970 | Brown et al. | 29/592.1 |
| 4,163,649 | A * | 8/1979 | Calvert | 95/275 |
| 4,930,664 | A * | 6/1990 | Ellison | 222/1 |
| 5,076,965 | A * | 12/1991 | Guelta et al. | 252/408.1 |
| 6,435,009 | B1 | 8/2002 | Tilley | |
| 6,784,988 | B2 | 8/2004 | Vijayakumar | |
| 6,848,297 | B2 | 2/2005 | Tilley | |
| 7,029,513 | B2 * | 4/2006 | Gardner et al. | 75/330 |
| 7,140,234 | B2 | 11/2006 | Tilley | |

(Continued)

OTHER PUBLICATIONS

Certitest, Product Information, Model 8127/8130 Automated Filter Testers, 2000.

(Continued)

*Primary Examiner*—Thomas P Noland
(74) *Attorney, Agent, or Firm*—Merek, Blackmon & Voorhees, LLC

(57) ABSTRACT

The preferred form of the present invention is directed to systems and methods used to test objects including but not limited to filters, respirator cartridges and filter media. The object to be tested is subjected to an aerosol challenge while the penetration percentage and resistance at a given flow are monitored to ensure that the object will function as desired. Preferably, the test object is challenged with a salt aerosol. However, any suitable aerosol may be used. A replenishment member is provided for automatically and continuously replenishing the reservoir of an aerosol generator. The replenishment member is configured such that there is no need for an operator to monitor the liquid level in the aerosol generator reservoir either during replenishment or at anytime while the apparatus is operated. The replenishment member of the preferred form of the present invention does not require interruption of the filter testing process to replenish the aerosol generator reservoir. The preferred form of the present invention supplies heated air to the aerosol generator reservoir to significantly reduce the liquid needed to be collected in the drip jar of the impactor. This feature prolongs the run time of the test system. A control device is operably associated with the heater to activate and deactivate the heater depending upon detection of pressurized gas supplied to the aerosol generator. This feature prevents the heater from irreparably damaging the test unit and/or the surrounding environment.

21 Claims, 3 Drawing Sheets

U.S. PATENT DOCUMENTS

| | | | |
|---|---|---|---|
| 2004/0119795 A1* | 6/2004 | Noolandi et al. | 347/85 |
| 2006/0013709 A1* | 1/2006 | Hudson et al. | 417/411 |
| 2006/0238757 A1* | 10/2006 | Silcott | 356/338 |
| 2009/0209877 A1* | 8/2009 | Zhang et al. | 600/529 |

OTHER PUBLICATIONS

Certitest, Operation and Service Manual, Model 8127?8130 Automated Filter Tester, Revision H, Jan. 2006.

Model 8118A Salt Aerosol Generator, Instruction Manual, Jan. 2004.

Operator's Manual for the TDA-100P Penetrometer.

Brochure on TDA-100S Automatic Filter Tester.

TSI Particle Technology, 2005.

Bulletin E-22, Flotect Model V6 Flow Switch.

Omegaflux AHP Series In-Line Heaters, Instruction Sheet, M2157/0495.

Flexflo Model A-1600, Peristaltic Injection Pump Operating Manual, Blue-White Industries, Ltd., Nov. 2004.

* cited by examiner

METHOD AND APPARATUS FOR TESTING AN OBJECT

FIELD OF THE INVENTION

The preferred form of the present invention is directed to systems and methods used to test objects including but not limited to filters, respirator cartridges, filter media and protective devices including protective masks, protective suits and other protective gear. The object to be tested is subjected to an aerosol challenge while the penetration percentage and/or resistance at a given flow are monitored to ensure that the object will function as desired. Preferably, the test object is challenged with a salt aerosol. However, any suitable aerosol may be used.

BACKGROUND OF THE INVENTION

Automated filter testers for testing filters, respirator cartridges and filter media have been previously developed. One such automated filter tester is the CERTITEST® filter tester manufactured by TSI incorporated. According to TSI, the CERTITEST® Models 8127 and 8130 are automated filter testers designed to test filters, respirator cartridges and filter media. Model 8127 uses an oil aerosol while Model 8130 uses either an oil aerosol or a salt aerosol. The Model 8127 and 8130 monitor filter penetration and resistance over a range of filter flows. Models 8127 and 8130 have significant limitations. Specifically, the aerosol generator in each of Models 8127 and 8130 must be manually replenished with liquid used to create the test aerosol. This requires that the liquid level in the aerosol generator be monitored. Further, the filter tester must be shutdown while the liquid in the aerosol generator is replenished, i.e., the filter tester cannot be used to test filters or any other device while the liquid supply for the aerosol generator is being replenished. Another limitation on Models 8127 and 8130 concerns the drip jar or collector that is associated with the impactor. More specifically, once a pressurized gas is introduced in the liquid solution (either oil or salt) in the aerosol generator, the test aerosol is created. The test aerosol is subjected to an impactor to refine the test aerosol in an effort to provide an optimum test aerosol to challenge the object to be tested. A drip jar is associated with the impactor to collect liquid particles descending downwardly after the test aerosol strikes the impactor. The drip jar or collector must be frequently emptied. Once again, the filter tester cannot be used to test filters or any other device while the drip jar or collector is being emptied. Models 8127 and 8130 also require a separate mixing chamber downstream of the aerosol generator for mixing the test aerosol with heated dilution air downstream of the aerosol generator.

Other automated filter testers include the TDA-100 series testers manufactured by Air Techniques International, a division of Hamilton Associates, Inc. The TDA-100 series testers use a salt aerosol and an oil aerosol depending upon the model to challenge a test object. The liquid reservoir of the aerosol is visible from the exterior of the cabinet housing through a window. The reservoir of the aerosol generator includes a pair of lines that indicate the maximum and minimum levels of liquid (i.e., oil solution or salt solution) to be maintained in the reservoir. Accordingly, the operator must continuously monitor the liquid level of the reservoir. When the liquid needs to be replenished, the pressurized gas normally used to create the test aerosol is diverted to a supply reservoir to direct a liquid to the reservoir of the aerosol generator to maintain the proper liquid level in the reservoir of the aerosol generator. While the refilling process is initiated by an operator pressing an external button on the test unit, the operator must continuously monitor the liquid level while the reservoir of the aerosol generator is being refilled or replenished with liquid. The TDA-100 series testers cannot test any objects while the reservoir of the aerosol is being refilled. In addition, the operator must monitor the aerosol generator reservoir during filtering to determine when to refill the reservoir.

OBJECTS AND SUMMARY OF THE INVENTION

An object of a preferred embodiment of the present invention is to provide a novel and unobvious apparatus and/or process for testing objects including but not limited to filters, respirator cartridges, filter media and protective devices including protective masks, protective suits and other protective gear.

Another object of a preferred embodiment of the present invention is to provide an apparatus and method for testing an object that automatically replenishes the reservoir of the aerosol generator.

A further object of a preferred embodiment of the present invention is provide an apparatus and method for testing an object that is capable of automatically replenishing the aerosol generator reservoir with a fluid while simultaneously challenging a test object with an aerosol.

Still a further object of a preferred embodiment of the present invention is provide an apparatus and method for testing an object that is capable of automatically replenishing the aerosol generator reservoir with a fluid while at the same time that a pressurized liquid is directed into the reservoir of the aerosol generator to create an aerosol.

Yet still a further object of a preferred embodiment of the present invention is to provide an apparatus and method for testing an object that is capable of automatically replenishing the aerosol generator reservoir with a liquid without the need for an operator to monitor the liquid level in the aerosol generator reservoir either during replenishment or at any other time while the apparatus is operated.

Yet another object of a preferred embodiment of the present invention is to provide an apparatus and method for testing an object that significantly reduces the volume of excess liquid that is created and required to be collected when a test aerosol strikes an impactor.

Still a further object of a preferred embodiment of the present invention is to provide a method and apparatus for testing an object that heats a pressurized gas prior to entry into the aerosol generator to significantly reduce the volume of excess liquid that is created when a test aerosol strikes an impactor downstream of the aerosol generator.

Yet still a further object of a preferred embodiment of the present invention is to provide a method and apparatus for testing an object that automatically activates and deactivates a heater to heat a pressurized gas prior to entry into an aerosol generator depending on the flow or lack thereof of the pressurized gas.

A further object of a preferred embodiment of the present invention is to provide an apparatus for testing an object that does not require highly skilled technicians to operate the same.

Another object of a preferred embodiment of the present invention is to provide an apparatus for testing a filter that can be run for considerably longer periods of time than previously developed filter testers without the need for operator intervention.

It must be understood that no one embodiment of the present invention need include all of the aforementioned objects of the present invention. Rather, a given embodiment may include one or none of the aforementioned objects. Accordingly, these objects are not to be used to limit the scope of the claims of the present invention.

In summary, one embodiment of the present invention is directed to an apparatus for testing an object including a generator for generating an aerosol to challenge the object. The generator includes a reservoir containing a liquid. A conduit is operably connected to the generator for directing a pressurized gas to the reservoir containing the liquid to create an aerosol for challenging the object. A replenishment member replenishes the reservoir with a liquid at the same time that a pressurized gas is directed into the reservoir of the generator.

Another embodiment of the present invention is directed to an apparatus for testing an object. The apparatus includes a generator for generating an aerosol to challenge the object. The generator includes a reservoir containing a liquid. A conduit is operably connected to the generator for directing a pressurized gas into the reservoir containing the liquid to create an aerosol for challenging the object. A heater is operably associated with the conduit for heating the pressurized gas directed into the reservoir.

A further embodiment of the present invention is directed to an apparatus for testing an object. The apparatus includes a generator for generating an aerosol to challenge the object. The generator includes a reservoir containing a liquid. A conduit is operably connected to the generator for directing a pressurized gas to the reservoir containing the liquid to create an aerosol for challenging the object. A replenishment member is provided for replenishing the reservoir with a liquid at the same time that liquid aerosolizes are generated.

Still anther embodiment of the present invention is directed-to an apparatus for testing an object including a generator for generating an aerosol to challenge the object. The generator includes a generator reservoir containing a liquid. A conduit is operably connected to the generator for directing a pressurized gas to the generator reservoir containing the liquid to create an aerosol for challenging the object. An automatic replenishment member for automatically replenishing the reservoir with a liquid such that no operator monitoring of liquid replenishment of the generator reservoir is required.

Yet another embodiment of the present invention is directed to a method for testing an object including the steps of: (a) providing an aerosol generator for generating an aerosol to challenge the object, the generator including a reservoir containing a liquid; (b) providing a conduit operably connected to the generator for directing a pressurized gas to the reservoir containing the liquid to create an aerosol for challenging the object; (c) directing a pressurized gas into the reservoir of the aerosol generator; and, (d) during at least a portion of step (c), replenishing the reservoir with a liquid.

Still yet another object of a preferred embodiment of the present invention is directed to a method for testing an object including the steps of: (a) providing an aerosol generator for generating an aerosol to challenge the object, the aerosol generator including a reservoir containing a liquid; (b) directing a pressurized gas into the reservoir containing the liquid to create an aerosol for challenging an object; and, (c) heating the pressurized gas prior to entry into the aerosol generator to cause liquid droplets forming the aerosol to evaporate.

DETAILED DESCRIPTION OF THE PREFERRED EMBODIMENT OF THE INVENTION

The most preferred form of the invention will now be described with reference to FIGS. 1-4. The appended claims are not limited to the most preferred embodiment and no term used herein is to be given a meaning other than its ordinary meaning unless expressly stated otherwise.

FIGS. 1 through 4

Figure 1:
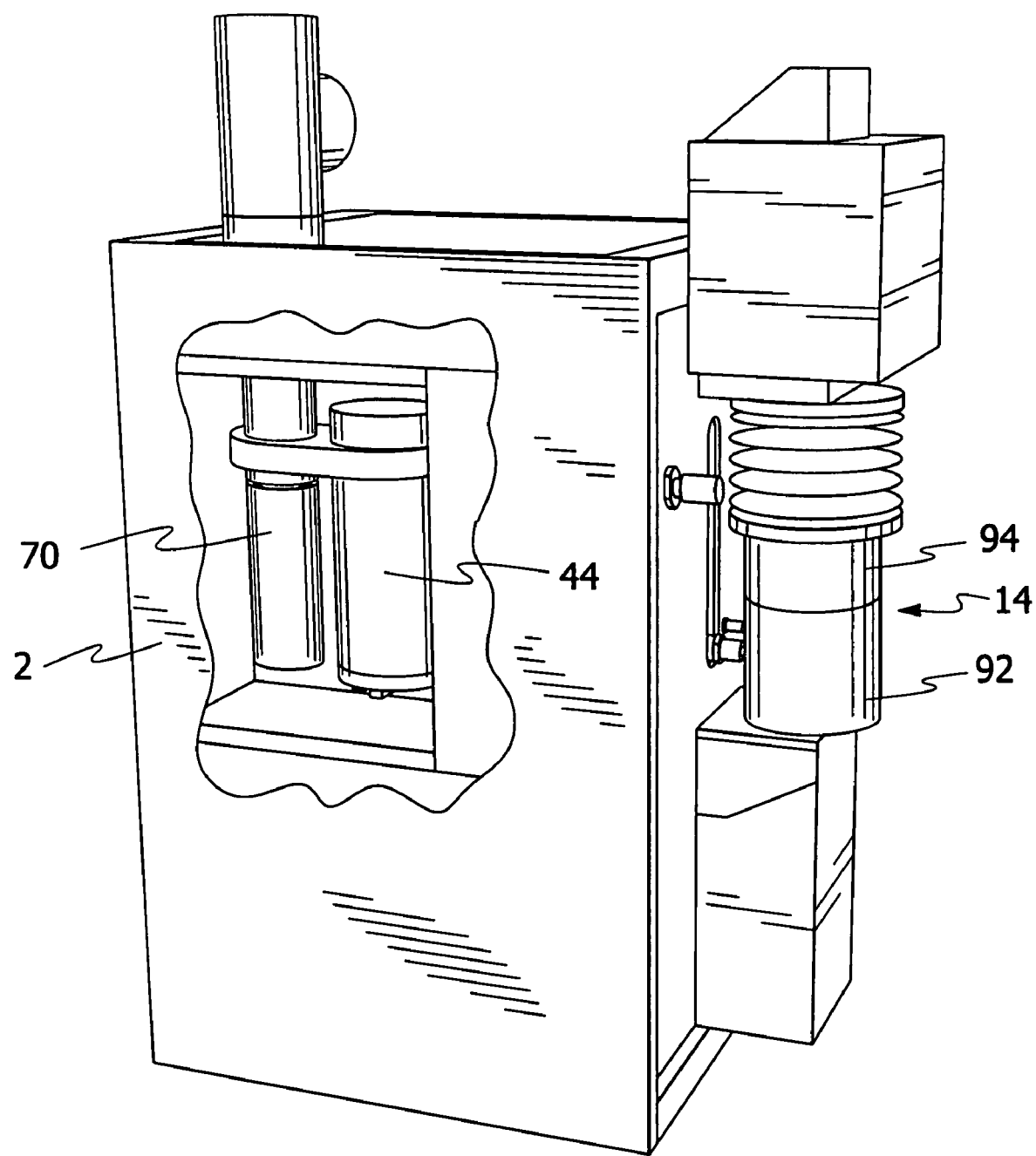
FIG. 1 is a fragmentary perspective view of an apparatus formed in accordance with the most preferred embodiment of the present invention.
Figure 2:
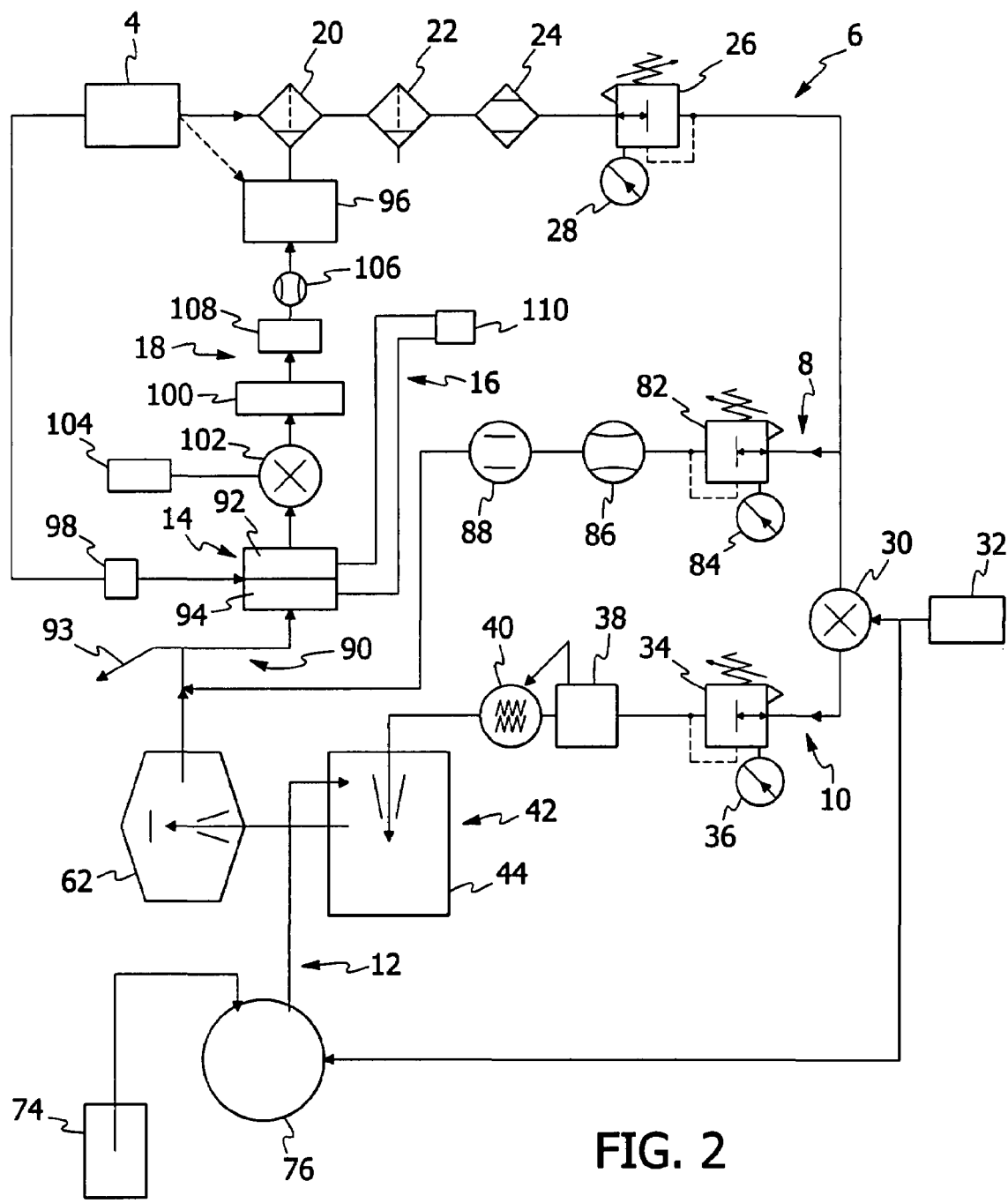
FIG. 2 is a schematic of a flow diagram formed in accordance with the most preferred embodiment of the present invention.

Referring to FIGS. 1 to 4, a testing unit A for testing objects including but not limited to filters, respirator cartridges, filter media and protective devices including protective masks, protective suits and other protective gear is illustrated in one of many possible configurations. Referring to FIGS. 1 and 2, testing unit A includes a housing 2, a source of pressurized air 4, an air preparation flow path 6, a dilution air flow path 8, an aerosol generation flow path 10, an aerosol generation solution replenishment flow path 12, chuck assembly 14, resistance detection flow path 16 and penetration and rate detection flow path 18. It will be noted that the chuck assembly 14 may need to be modified depending on the test object.

The compressed source of air 4 is preferably external to housing 2 and is connected thereto in any suitable manner to supply pressurized air to housing 2. While air is the preferred pressurized fluid, it will be readily appreciated that any suitable fluid may be used. Upon entry into housing 2, the pressurized air flows through an air preparation flow path 6 that preferably includes a pair of filters 20 and 22 and a dryer 24 as shown in FIG. 2. Filter 20 is preferably a general filter while filter 22 is an oil filter. Dryer 24 is preferably a membrane dryer. Filters 20 and 22 remove impurities from the pressurized air while dryer 24 reduces the moisture level in the pressurized air thereby dropping the due point to approximately 30 to 40 degrees. A pressure regulator 26 regulates the air pressure through the air preparation flow path 6. A pressure gauge 28 may be provided to detect and report the air pressure passing through air preparation flow path 4.

Preferably, an on/off control valve 30 controls the flow of pressurized air to the aerosol generation flow path 10. Control valve 30 can be a solenoid valve or any other suitable device. When control valve 30 is open, pressurized air that has been suitably prepared by the air preparation flow path 6 is directed through the aerosol generation flow path 10. Conversely, when valve 30 is closed, pressurized air does not pass to aerosol generation flow path 10. A relay 32 is operably connected to control valve 30 to open and close valve 30. A microprocessor will cause relay 32 to open valve 30 when an object is tested. Conversely, valve 30 is closed by a microprocessor when no object is tested.

Aerosol generation flow path 10 includes a pressure regulator 34 for regulating the air pressure in aerosol generation flow path 10. A pressure gauge 36 may be provided to detect and report the air pressure in aerosol generation flow path 10. Aerosol generation flow path 10 further includes a flow switch 38 upstream of and operably connected to heater 40. Preferably, heater 40 heats the pressurized air to between 140° F. and 190° F. prior to entry in aerosol generator 42. Most preferably, the pressurized air is heated to approximately 167° F. Heater 40 is preferably an in-line heater. An example of a suitable in-line heater is the OMEGALUX® AHP series in-line heaters. However, it should be noted that the present invention is not limited to an in-line heater let alone the specific type described above. Flow switch 38 activates and deactivates heater 40. More specifically, when flow switch 38 detects pressurized air flow, heater 40 is turned on to heat the pressurized air to the desired temperature. Conversely, when no pressurized air is detected by flow switch 38, heater 40 is turned off thereby preventing heater 40 from damaging testing unit A and/or the surrounding environment. An example of a suitable flow switch is the FLOTECT® Model V6 flow switch. Once again, the reference to this flow switch is merely to provide an example of a flow switch and does not in any way limit the present invention to this specific type of flow switch.

Figure 3:
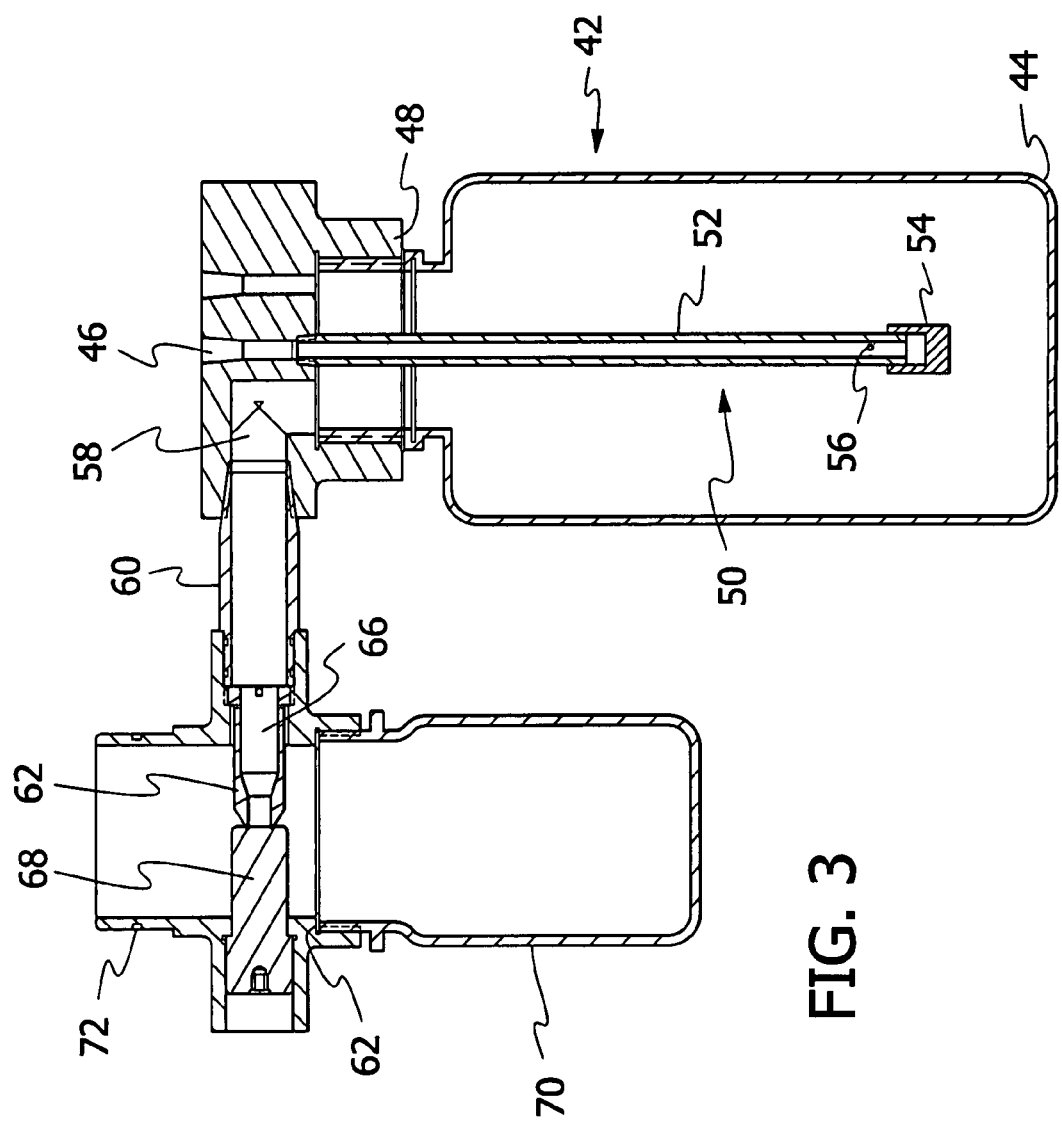
FIG. 3 is a cross-sectional view of the aerosol generator and impactor assemblies formed in accordance with the most preferred embodiment of the present invention.

Referring to FIGS. 2 and 3, heated pressurized air is directed into reservoir 44 of aerosol generator 42 through inlet 46 formed in aerosol generator cap 48. Reservoir 44 preferably includes a saline solution having a salinity of approximately 1.5% to 10% and most preferably of approximately 2% to 2.5%. However, it will be readily appreciated that the concentration may be modified as desired. Further, challenge liquids other than a saline solution may be used including but not limited to oil. The heated pressurized air passes into nozzle 50. Nozzle 50 includes a tube 52 and an end cap 54. Preferably, four nozzle shaped openings 56 (only one of which is shown) are uniformly spaced around tube 52 above end cap 54. Heated air exits openings 56 and creates an aerosol challenge.

Referring to FIG. 3, the aerosol challenge exits aerosol generator 42 through pathway 58 formed in generator cap 54. Connecting tube 60 connects aerosol generator 42 to impactor 62 in a fluid tight manner. Impactor 62 includes an inlet conduit 64 having a bore 66 extending therethrough. The size of bore 66 is reduced directly adjacent impactor plate 68. This configuration of bore 66 increases the flow rate of the aerosol prior to striking impactor plate 68. Impactor 62 includes a drip jar 70. Drip jar 70 collects excess liquid descending downwardly after the aerosol strikes impactor plate 68. Aerosol refined by impactor 62 exits through outlet 72. The introduction of heated pressurized air into the aerosol generator 42 causes excess liquid of the aerosol to evaporate prior to exiting aerosol generator 42. This is an advantageous feature of the preferred form of the present invention as it significantly reduces the liquid collected in drip jar 70. Accordingly, test unit A can be run for significantly longer periods of time, i.e., the drip jar 70 of the test unit A does not need to be emptied as frequently as the drip jars in previously developed test units.

Referring to FIG. 2, aerosol solution replenishment flow path 12 includes a reservoir 74. The reservoir is preferably mounted to the exterior of housing 2 so that it can be readily refilled as needed without shutting down test unit A. The reservoir can contain distilled water, a saline solution or other suitable liquid solution. Aerosol solution replenishment flow path 12 further includes a replenishment member 76 connected at one end to reservoir 74 and the other end to reservoir 44. Preferably, replenishment member 76 is a pump and most preferably is a peristaltic pump. An example of a suitable pump is the peristaltic injection pump, Model A-1600 manufactured by Blue-White Industries, Ltd. Relay 32 turns replenishment member 76 on and off. A microprocessor controls relay 32. Specifically, the microprocessor will cause relay 32 to activate replenishment member 76 when pressurized air is supplied to aerosol generation flow path 12. Conversely, the microprocessor will cause relay 32 to deactivate replenishment member 76 when no pressurized air is supplied to the aerosol generation flow path 10.

Replenishment member 76 is preferably designed such that the rate of fluid pumped from reservoir 74 to reservoir 44 maintains the liquid in reservoir 44 at a predetermined level, i.e., as liquid from reservoir 44 is used in creating the aerosol challenge, replenishment member 76 automatically and continuously supplies the appropriate amount of liquid to reservoir 44 to maintain the liquid level in reservoir 44 at a desired level without the need for operator supervision. Relay 32 preferably activates valve 30 and pump 76 simultaneously. More specifically, unlike previously developed testers, the reservoir generator need not be monitored to ensure that the solution is maintained at a desired level. Moreover, unlike previously developed testers, the preferred embodiment of the present invention need not be shutdown to refill the aerosol generator. It should be noted that the replenishment member 76 may be turned on for the entire time that pressurized air is directed to aerosol generator 42. Further, replenishment member 76 may be turned on for only a portion of the time that pressurized air is directed to aerosol generator 42.

Figure 4:
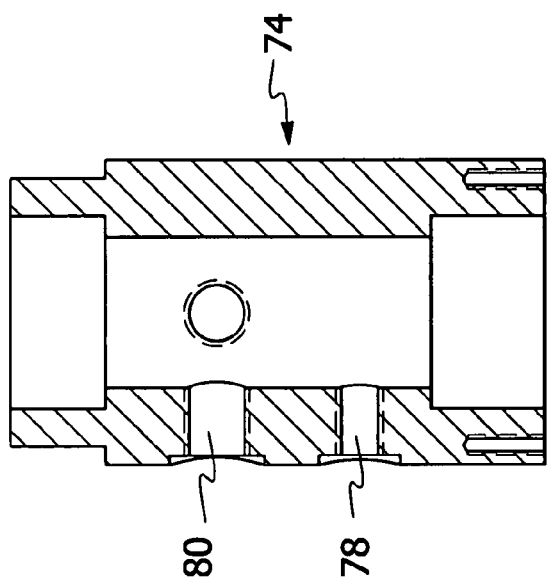
FIG. 4 is a cross-sectional view of an exhaust tube formed in accordance with a most preferred embodiment of the present invention.

Once the aerosol is refined by impactor 62, it exits through outlet 72 and is directed into exhaust tube 74 (shown in FIG. 4) connected to and extending upwardly from impactor 62. Preferably, outlet 72 extends into exhaust tube 74. Referring to FIG. 4, exhaust tube 74 includes two side ports 78 and 80. Referring to FIG. 2, the dilution air flow path 8 provides pressurized air into the exhaust tube 74 through port 78 to dilute the aerosol passing upwardly through exhaust tube 74. The dilution air flow path 8 may include a pressure regulator 82, a pressure gauge 84, a flow meter 86 and ionizer 88. Pressure regulator 82 controls the air pressure in dilution air flow path 8. Pressure gauge 84 detects and reports the air pressure in dilution flow path 8. Ionizer 88 neutralizes the static charge in the air stream.

A fluid line 90, shown schematically in FIG. 2, connects port 80 to chuck assembly 14 to direct the diluted aerosol through the object to be tested. Excess aerosol is exhausted from test unit A through the opening in the upper portion of exhaust tube 74. The exhaust is shown schematically in FIG. 2 and line 93. Chuck assembly 14 can be formed in a conventional manner. Specifically, chuck assembly 14 can include a lower element 92 that supports the object to be challenged with aerosol. The upper element 94 is moveable between a test position and an inactive position. In the test position, the upper element 94 engages the lower element 92 in a well known fluid tight manner. During a test, vacuum pump 96 pulls the aerosol challenge downwardly through chuck assembly 14 to subject the test object to the aerosol challenge. The vacuum pump 96 is driven by compressed air source 4. In the inactive position, the upper element 94 is raised to allow a test object to be removed from or positioned on lower element 92. Compressed air source 4 is preferably used to raise and lower upper element 94. More specifically, a solenoid valve 98 selectively directs pressurized air to a pair of ports in a pneumatic cylinder to raise and lower upper element 94 in a well known manner.

After the aerosol challenge passes through the object to be tested, it is pulled through photometer 100 by vacuum pump 96. Photometer 100 is used in a well known manner to determine the percentage of penetration of the aerosol through the test object. A control valve 102, preferably a three-way solenoid valve, connects and disconnects the chuck assembly to the photometer 100. Specifically, when an object is being tested valve 102 is positioned such that vacuum pump 96 pulls the aerosol challenge passing through the test object through photometer 100. When no test is being performed, solenoid valve 102 is positioned such that vacuum pump 96 pulls air through filter 104 and photometer 100. While control valve 102 is preferably a three-way solenoid valve, any suitable device may be used.

Flow meter 106 is downstream of filter 108 and photometer 100. Filter 108 prevents flow meter 106 from being subject to the particles in the aerosol. The flow meter detects the flow rate and is used in conjunction with the resistance measurement of the test object to determine the suitability of the test object. Resistance of the test object is determined by the resistance flow path 16. The resistance flow path 16 includes a pressure transducer 110 connected upstream and downstream of the object to be tested to determine the resistance of the object to be tested in a well known manner.

A display panel may be provided on housing 2 to display digitally or otherwise the percent of penetration and the resistance at a particular flow rate as is well known. Further, the display panel may include indicators for indicating the following: (1) the unit is ready for testing; (2) the test object failed; and, (3) a system fault exists. The display panel may also include a plurality of functions keys to select or changes options as is well known.

Preferably, all of the elements referred to above are disposed in housing 2 with the exceptions of reservoir 74 and compressed air source 4. Further, a microprocessor may be used to control various elements of test unit A including relay 32, valves 30, 98 and 102 and pressure regulators 26, 34 and 82.

While this invention has been described as having a preferred design, it is understood that the preferred design can be further modified or adapted following in general the principles of the invention and including but not limited to such departures from the present invention as come within the known or customary practice in the art to which the invention pertains. The claims are not limited to the preferred embodiment and have been written to preclude such a narrow construction using the principles of claim differentiation.

We claim:

1. An apparatus for testing an object, said apparatus comprising:
   (a) a generator for generating an aerosol to challenge said object; said generator including a reservoir containing a liquid;
   (b) a conduit operably connected to said generator for directing a pressurized gas to said reservoir containing the liquid to create an aerosol for challenging said object;
   (c) a replenishment member for replenishing said reservoir with a liquid at the same time that a pressurized gas is directed into said reservoir of said generator to create an aerosol for challenging said object; and,
   (d) a detector for detecting at least one characteristic relating to said object.

2. An apparatus as set forth in claim 1, wherein:
   (a) said generator generates a salt aerosol.

3. An apparatus as set forth in claim 1, wherein:
   (a) said replenishment member is a pump.

4. An apparatus as set forth in claim 1, further including:
   (a) means for activating said replenishment member to replenish said reservoir when a pressurized gas is directed into said reservoir of said generator.

5. An apparatus as set forth in claim 1, wherein:
   (a) said object is a filter.

6. An apparatus as set forth in claim 5, wherein:
   (a) said detector is a light scattering chamber for detecting penetration of said filter by said challenge aerosol.

7. An apparatus as set forth in claim 1, further including:
   (a) a heater for heating the pressurized gas directed to said reservoir of said generator.

8. An apparatus as set forth in claim 7, wherein:
   (a) said generator and said heater are housed in a cabinet.

9. An apparatus as set forth in claim 7, further including:
   (a) a dryer for drying the pressurized gas, said heater being located downstream of said dryer.

10. An apparatus as set forth in claim 9, wherein:
    (a) said dryer is a membrane dryer.

11. An apparatus as set forth in claim 7, further including:
    (a) a control member for activating said heater only when a pressurized gas is directed to said generator and deactivating said heater when the pressurized gas is not directed to said generator.

12. An apparatus as set forth in claim 1, wherein:
    (a) said pressurized gas is pressurized air.

13. An apparatus for testing an object, said apparatus comprising:
    (a) a generator for generating an aerosol to challenge said object; said generator including a reservoir containing a liquid;
    (b) a conduit operably connected to said generator for directing a pressurized gas into said reservoir containing the liquid to create an aerosol for challenging said object;
    (c) a heater operably associated with said conduit for heating said pressurized gas directed into said reservoir; and,
    (d) a detector for detecting at least one characteristic relating to said object.

14. An apparatus as set forth in claim 13, wherein:
    (a) said heater is an in-line heater.

15. An apparatus as set forth in claim 14, further including:
    (a) a control member for activating said heater only when a pressurized gas is directed to said generator and deactivating said heater when the pressurized gas is not directed to said generator.

16. An apparatus as set forth in claim 13, wherein:
    (a) said heater heats pressurized air to between 140° F. and 190°F.

17. An apparatus for testing an object, said apparatus comprising:
    (a) a generator for generating an aerosol to challenge said object; said generator including a reservoir containing a liquid;
    (b) a conduit operably connected to said generator for directing a pressurized gas to said reservoir containing the liquid to generate an aerosol for challenging said object; and,
    (c) a replenishment member for replenishing said reservoir with a liquid at the same time that an aerosol is generated;
    (d) means for activating said replenishment member to replenish said reservoir with a liquid when the pressurized gas is directed to said reservoir; and,
    (e) a detector for detecting at least one characteristic relating to said object.

18. An apparatus as set forth in claim 17, wherein:
(a) said replenishing liquid is a saline solution to maintain a predetermined concentration in said reservoir.

19. An apparatus for testing an object, said apparatus comprising:
(a) a generator for generating an aerosol to challenge said object; said generator including a generator reservoir containing a liquid;
(b) a conduit operably connected to said generator for directing a pressurized gas to said generator reservoir containing the liquid to create an aerosol for challenging said object; and,
(c) an automatic replenishment member for automatically replenishing said reservoir with a liquid such that no operator monitoring of liquid replenishment of said generator reservoir is required; and,
(d) a detector for detecting at least one characteristic relating to said object.

20. A method for testing an object, said method comprising the steps of:
(a) providing an aerosol generator for generating an aerosol to challenge said object, said generator including a reservoir containing a liquid;
(b) providing a conduit operably connected to said generator for directing a pressurized gas to said reservoir containing the liquid to create an aerosol for challenging said object;
(c) providing a detector for detecting at least one characteristic relating to said object;
(d) directing a pressurized gas into said reservoir of said aerosol generator; and,
(e) during at least a portion of step (d), replenishing said reservoir with a liquid; and,
(f) detecting at least one characteristic relating to said object.

21. A method for testing an object, said method comprising the steps of:
(a) providing an aerosol generator for generating an aerosol to challenge said object, said aerosol generator including a reservoir containing a liquid;
(b) directing a pressurized gas into said reservoir containing the liquid to create an aerosol for challenging an object;
(c) providing a detector for detecting at least one characteristic relating to said object
(d) heating said pressurized gas prior to entry into said aerosol generator to cause liquid droplets forming the aerosol to evaporate; and,
(e) detecting at least one characteristic relating to said object.

* * * * *